(12) United States Patent
Hoggarth et al.

(10) Patent No.: US 10,835,118 B2
(45) Date of Patent: Nov. 17, 2020

(54) SYSTEMS AND METHODS FOR PUPIL SIZE DETECTION

(71) Applicant: Johnson & Johnson Vision Care, Inc., Jacksonville, FL (US)

(72) Inventors: Steven Hoggarth, Cary, NC (US); Tao Zhang, Fremont, CA (US); Adam Toner, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 240 days.

(21) Appl. No.: 16/150,189

(22) Filed: Oct. 2, 2018

(65) Prior Publication Data
US 2020/0100670 A1 Apr. 2, 2020

(51) Int. Cl.
*G02C 7/08* (2006.01)
*A61B 3/11* (2006.01)
*A61B 3/15* (2006.01)
*A61B 3/00* (2006.01)

(52) U.S. Cl.
CPC ............ *A61B 3/112* (2013.01); *A61B 3/0025* (2013.01); *A61B 3/156* (2013.01)

(58) Field of Classification Search
CPC .......... G02C 7/04; G02C 7/081; G02C 7/085; G02C 7/041
USPC .......... 351/159.01, 159.03, 159.39
See application file for complete search history.

(56) References Cited

U.S. PATENT DOCUMENTS

2014/0240657 A1* 8/2014 Pugh ............... A61F 2/1624
351/159.03

* cited by examiner

*Primary Examiner* — Hung X Dang

(57) ABSTRACT

The present disclosure relates to sensor systems for electronic ophthalmic devices. In certain embodiments, the sensor systems may comprise a selection layer configured to reject light from the eye within a first range of incident angles and allow light from the eye within a second range of incident angles to pass through the selection layer. The sensor system may comprise a plurality of photodiodes disposed below the selection layer and configured to detect the light from the eye within the second range of incident angles that is allowed to pass through the selection layer. The sensor system may comprise an output circuit electrically coupled to the plurality of photodiodes and configured to output a signal indicative of which photodiode of the plurality of photodiodes detected the light.

66 Claims, 15 Drawing Sheets

| Unit Cell Side View | | | | | |
|---|---|---|---|---|---|
| LM | LM | LM | LM | | |
| M6 | | | | | |
| M5 | | | | | |
| M4 | | | | | |
| M3 | | | | | |
| M2 | | | | | |
| M1 | | | | | |
| | PD1 | PD2 | PD3 | NU | PD4 |

*FIG. 6A*

| Unit Cell Side View | | | | | |
|---|---|---|---|---|---|
| AM | LM,PD1 | LM,PD2 | LM,PD3 | NU | PD4 |
| AM | LM,PD2 | LM,PD2 | LM,PD2 | NU | PD4 |
| AM | LM,PD3 | LM,PD3 | LM,PD3 | NU | PD4 |
| AM | LM,PD4 | LM,PD4 | LM,PD4 | NU | PD4 |
| AM | AM | AM | AM | AM | AM |

*FIG. 6B*

SYSTEMS AND METHODS FOR PUPIL SIZE DETECTION

BACKGROUND OF THE DISCLOSURE

1. Field of the Disclosure

The present disclosure relates to electronic ophthalmic devices, such as wearable lenses, including contact lenses, implantable lenses, including intraocular lenses (IOLs) and any other type of device comprising optical components, and more particularly, to sensors and associated hardware and software for detecting changes in eye characteristics to activate and control electronic ophthalmic devices.

2. Discussion of the Related Art

Ophthalmic devices, such as contact lenses and intraocular lenses, currently are utilized to correct vision defects such as myopia (nearsightedness), hyperopia (farsightedness), presbyopia and astigmatism. However, properly designed lenses incorporating additional components may be utilized to enhance vision as well as to correct vision defects.

Ophthalmic devices may incorporate a lens assembly having an electronically adjustable focus to augment or enhance performance of the eye. The use of embedded electronics in a lens assembly introduces a potential requirement for communication with the electronics, for a method of powering and/or re-energizing the electronics, for interconnecting the electronics, for internal and external sensing and/or monitoring, and for control of the electronics and the overall function of the lens.

Conventional contact lenses are polymeric structures with specific shapes to correct various vision problems as briefly set forth above. To achieve enhanced functionality, various circuits and components have to be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality.

For example, electronic and/or powered contract lenses may be designed to provide enhanced vision via zoom-in and zoom-out capabilities, or simply modify the refractive capabilities of the lenses. Electronic and/or powered contact lenses may be designed to enhance color and resolution, to display textural information, to translate speech into captions in real time, to offer visual cues from a navigation system, and to provide image processing and internet access. The lenses may be designed to allow the wearer to see in low-light conditions. The properly designed electronics and/or arrangement of electronics on lenses may allow for projecting an image onto the retina, for example, without a variable-focus optic lens, provide novelty image displays and even provide wakeup alerts. Alternately, or in addition to any of these functions or similar functions, the contact lenses may incorporate components for the noninvasive monitoring of the wearer's biomarkers and health indicators.

In addition, because of the complexity of the functionality associated with a powered lens and the high level of interaction between its components, there is a need to coordinate and control the overall operation of the electronics and optics.

SUMMARY OF THE DISCLOSURE

The present disclosure relates to an ophthalmic system. The ophthalmic system may comprise an ophthalmic device configured to be disposed within or upon an eye of a user; and a sensor system disposed in or on the ophthalmic device. "Upon" the eye may comprise in contact with the eye, disposed in a liquid in contact with the eye, disposed between an eyelid and the eye, at least partially disposed within the eye, resting on the eye, and/or the like. The sensor system may comprise: a selection layer configured to receive light from (e.g., reflected from or transmitted though) the eye, wherein the selection layer is configured to reject light from the eye within a first range of incident angles and allow light from the eye within a second range of incident angles to pass through the selection layer; a plurality of photodiodes disposed below the selection layer and configured to detect the light from the eye that is allowed to pass through the selection layer; and a processor operably connected to the sensor and configured for: receiving first data indicative of first light from the eye that passed through the selection layer; receiving second data indicative of second light from the eye that passed through the selection layer; comparing the first data and the second data; and determining a characteristic of the eye based on the comparison of the first data and the second data.

The present disclosure relates to a method for determining a characteristic of an eye of a user of an ophthalmic device. Certain methods may comprise receiving first data indicative of first light from (e.g., reflected from or transmitted through) an eye that passed through a selection layer, wherein the selection layer is configured to reject light from the eye within a first range of incident angles and allow light from the eye within a second range of incident angles to pass through the selection layer to one or more of a plurality of photodiodes, wherein the selection layer and the plurality of photodiodes are comprised in an ophthalmic device disposed in or on the eye; receiving second data indicative of second light from the eye that passed through the selection layer; comparing the first data and the second data; and determining a characteristic of the eye based on the comparison of the first data and the second data.

The present disclosure relates to a sensor. The sensor may comprise a selection layer configured to be disposed in or on an ophthalmic device to receive light from (e.g., reflected from or transmitted through) an eye, wherein the selection layer is configured to reject light from the eye within a first range of incident angles and allow light from the eye within a second range of incident angles to pass through the selection layer; a plurality of photodiodes disposed below the selection layer and configured to detect the light from the eye within the second range of incident angles that is allowed to pass through the selection layer; and an output circuit electrically coupled to the plurality of photodiodes and configured to output a signal indicative of which photodiode of the plurality of photodiodes detected the light.

The present disclosure relates to a method for operating a sensor. Certain methods may comprise rejecting, by a selection layer, light from (e.g., reflected from or transmitted through) an eye within a first range of incident angles, wherein the selection layer is disposed in or on an ophthalmic device; allowing, by the selection layer, light from the eye within a second range of incident angles to pass through the selection layer; detecting, by one or more of a plurality of photodiodes below the selection layer, the light from the eye within the second range of incident angles; and outputting, by an output circuit electrically coupled to the plurality of photodiodes, a signal indicative of which photodiode of the plurality of photodiodes detected the light.

BRIEF DESCRIPTION OF THE DRAWINGS

The foregoing and other features and advantages of the disclosure will be apparent from the following, more particular description of preferred embodiments of the disclosure, as illustrated in the accompanying drawings.

FIG. 6A is a side view illustrating placement of a plurality of photodiodes of an exemplary sensor in accordance with some embodiments of the present disclosure.

FIG. 6B is a top-down view illustrating placement of a plurality of photodiodes of an exemplary sensor in accordance with some embodiments of the present disclosure.

DETAILED DESCRIPTION OF THE PREFERRED EMBODIMENTS

Figure 1:
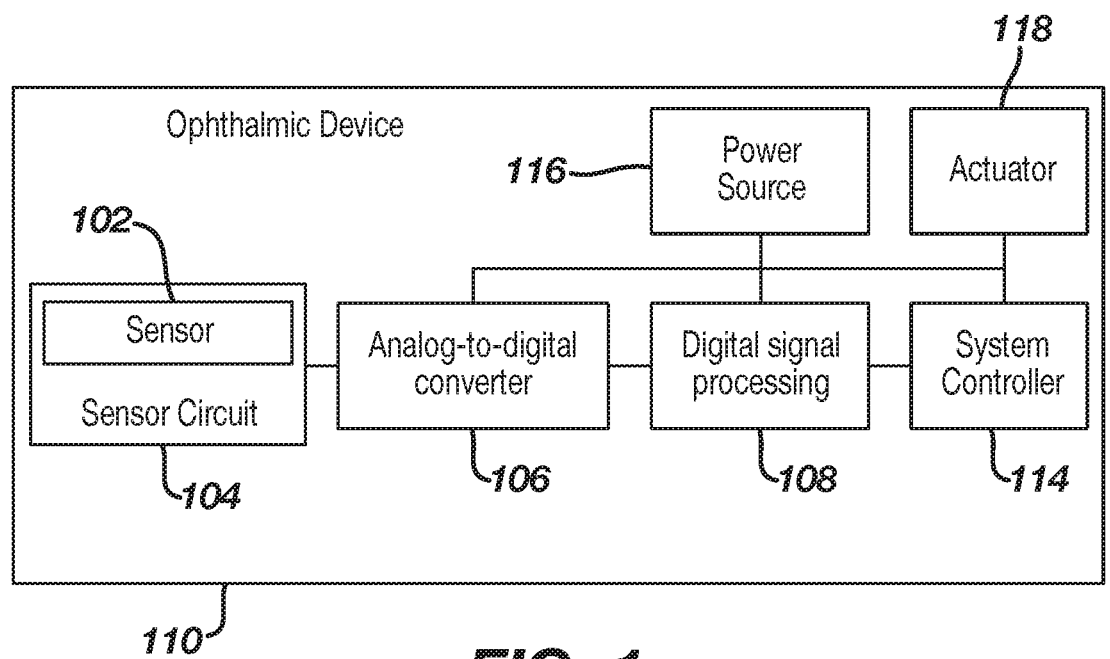
FIG. 1 illustrates an exemplary ophthalmic device comprising a sensor system in accordance with some embodiments of the present disclosure.

Ophthalmic devices may include implantable device and/or wearable devices, such as contact lenses. Conventional contact lenses are polymeric structures with specific shapes to correct various vision problems as briefly set forth above. To achieve enhanced functionality, various circuits and components may be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality as is explained herein.

Electronic and/or powered ophthalmic devices such as contact lenses may be designed to provide enhanced vision via zoom-in and zoom-out capabilities, and/or to modify the refractive capabilities of the lenses. Electronic and/or powered devices may be designed to enhance color and resolution, to display textural information, to translate speech into captions in real time, to offer visual cues from a navigation system, and to provide image processing and internet access. The devices may be designed to allow the user/wearer to see in low light conditions. The properly designed electronics and/or arrangement of electronics on devices (e.g., lenses) may allow for projecting an image onto the retina, for example, without a variable focus optic lens, provide novelty image displays and even provide wakeup alerts. Alternately, or in addition to any of these functions or similar functions, the ophthalmic devices (e.g., contact lenses, intraocular lenses) may incorporate components for the noninvasive monitoring of the wearer's biomarkers and health indicators. For example, sensors built into the ophthalmic devices (e.g., contact lenses, intraocular lenses) may allow a diabetic patient to keep tabs on blood sugar levels by analyzing components of the tear film without the need for drawing blood. In addition, an appropriately configured lens may incorporate sensors for monitoring cholesterol, sodium, and potassium levels, as well as other biological markers. This coupled with a wireless data transmitter could allow a physician to have almost immediate access to a patient's blood chemistry without the need for the patient to waste time getting to a laboratory and having blood drawn. In addition, sensors built into the ophthalmic devices (e.g., contact lenses, intraocular lenses) may be utilized to detect light incident on the eye to compensate for ambient light conditions or for use in determining blink patterns.

The powered or electronic ophthalmic devices of the present disclosure may comprise the necessary elements to correct and/or enhance the vision of patients with one or more of the above described vision defects or otherwise perform a useful ophthalmic function. In addition, the electronic contact lens may be utilized simply to enhance normal vision or provide a wide variety of functionality as described above. The electronic contact lens may comprise a variable focus optic lens, an assembled front optic embedded into a contact lens or just simply embedding electronics without a lens for any suitable functionality. The electronic lens of the present disclosure may be incorporated into any number of contact lenses as described above. In addition, intraocular lenses may also incorporate the various components and functionality described herein. However, for ease of explanation, the disclosure will focus on an electronic contact lens to correct vision defects intended for single-use daily disposability.

The present disclosure may be employed in a powered ophthalmic device comprising an electronic system, which actuates a variable-focus optic or any other device or devices configured to implement any number of numerous functions that may be performed. The electronic system includes one or more batteries or other power sources, power management circuitry, one or more sensors, clock generation circuitry, control algorithms and circuitry, and lens driver circuitry. The complexity of these components may vary depending on the required or desired functionality of the lens.

Control of an electronic or a powered ophthalmic lens may be accomplished through a manually operated external device that communicates with the lens, such as a hand-held remote unit. For example, a fob may wirelessly communicate with the powered lens based upon manual input from the wearer. Alternately, control of the powered ophthalmic lens may be accomplished via feedback or control signals directly from the wearer. For example, sensors built into the lens may sense signals indicative of iris movement (e.g., change in pupil size), ciliary muscle movement, i.e. contraction and relaxation, and/or the like to compensate for crystalline lens dysfunction or any other problems associated with visual acuity or eye disease. Based upon these signals, the powered ophthalmic lens may change state, for example, its refractive power, in order to either focus on a near object or a distant object.

Powered or electronic ophthalmic devices may have to account for the various changes in characteristics of an eye. More specifically, powered ophthalmic devices may need to detect changes in the pupil and/or iris of the eye.

The iris, or colored part of the eye, is the partition between the anterior and posterior chambers of the eye and it is made up of two muscles that regulate the size of the pupil to control the amount of light entering the eye. The dilator muscle opens the pupil and the sphincter muscle closes the pupil. The eye also has six extraoccular muscles that control the overall movement of the eye or eye globe. The sensing of changes in the pupil and/or iris may provide other or additional functionality for a powered or electronic ophthalmic lens. In accordance with the present disclosure, the circuitry is configured to detect, isolate and amplify changes in the size of the pupil and/or iris while filtering out noise.

FIG. 1 illustrates, in block diagram form, an ophthalmic device 100 disposed on the front surface of the eye or cornea 112, in accordance with one exemplary embodiment of the present disclosure. Although the ophthalmic device 100 is shown and described as a being disposed on the front surface of the eye, it is understood that other configurations, such as those including intraocular lens configuration may be used. In this exemplary embodiment, the sensor system may comprise one or more of a sensor 102, a sensor circuit 104, an analog-to-digital converter 106, a digital signal processor 108, a power source 116, an actuator 118, and a system controller 114. The sensor 102 as well as the other circuitry is configured to sense changes in the size of the pupil (e.g., or iris) and other characteristics (e.g., or the user, or the environment of the user).

In this exemplary embodiment, the sensor 102 may be at least partially embedded into the ophthalmic device 100. The sensor 102 may be disposed to sense changes in light from (e.g., reflected from or transmitted through) the eye. The pupil may absorb light, but light may be reflected from and/or transmitted through the iris, cornea, and/or other parts of the eye. The sensor 102 may be configured to generate an electrical signal indicative a change in the size of the pupil. As such, when the size of the pupil changes, the sensor 102 may sense changes in light from (e.g., reflected from or transmitted through) the eye. The changes may be related to changing angles and/or directions of the like that is detected by the sensor. Certain angles and/or directions of the light may indicative of and/or associated with corresponding sizes (e.g., diameters) of the pupil.

The sensor circuit 104 or sensor system may be configured to process signals received by the sensor 102. As an example, the sensor circuit 104 may be configured to amplify a signal to facilitate integration of small changes in signal level. As a further example, the sensor circuit 104 may be configured to amplify a signal to a useable level for the remainder of the system, such as giving a signal enough power to be acquired by various components of the sensor circuit 104 and/or the analog-to-digital converter 106. In addition to providing gain, the sensor circuit 104 may include other analog signal conditioning circuitry such as filtering and impedance matching circuitry appropriate to the sensor 102 and sensor circuit 104 output. The sensor circuit 104 may comprise any suitable device for amplifying and conditioning the signal output by the sensor 102. For example, the sensor circuit 104 may simply comprise a single operational amplifier or a more complicated circuit comprising one or more operational amplifiers.

As set forth above, the sensor 102 and the sensor circuit 104 are configured to capture and isolate signals indicative of characteristic of the eye (e.g., pupil size) and convert it to a signal usable ultimately by the system controller 114. The system controller 114 is preferably preprogrammed to recognize the various signals produced by changes in pupil size under various conditions. The system controller 114 may, in some cases, provide an appropriate output signal to the actuator 118. A change in pupil size may be used to determine other characteristics of the eye, such as accommodation. A change in pupil size may be used with other sensor information to determine a characteristic of the eye. For example, the sensor information may comprise an ambient light level, ciliary muscle contraction data, accelerometer data, impedance data, and/or the like. As another example, if the pupil has decreased in size (e.g., contracted) and ambient light levels have not increased, then it can be determined that the eye is changing to a near focus. A lens (e.g., or other active element) of the ophthalmic device may be activated to assist the user with adjusting to the near focus.

In this exemplary embodiment, the analog-to-digital converter 106 may be used to convert an analog signal output from the amplifier into a digital signal for processing. For example, the analog-to-digital converter 106 may convert an analog signal output from the sensor circuit 104 into a digital signal that may be useable by subsequent or downstream circuits, such as a digital signal processing system 108 or microprocessor. A digital signal processing system or digital signal processor 108 may be utilized for digital signal processing, including one or more of filtering, processing, detecting, and otherwise manipulating/processing sampled data to discern changes in light (e.g., reflected from or transmitted through the eye) due to changes in the pupil from noise and interference.

The digital signal processor 108 may be preprogrammed to recognize signals related to changes in the characteristic of the eye. The digital signal processor 108 may be implemented utilizing analog circuitry, digital circuitry, software and/or preferably a combination thereof. For example, various signals from the sensor 102 may be matched to corresponding changes in pupil size. The signals from the sensor 102 may comprise a signal representing an amount of light detected by one or more photodiodes of the sensor. The signals from the sensor 102 may comprise location information indicating a location of the photodiodes that detected a signal. For example, the location information may comprise a group number, row number, channel number, and/or the like indicative of a location of the photodiode detecting light. Each group number, row number, channel number, and/or the like may be associated with a direction and/or angle of light. Each group number, row number, channel number, and/or the like may be associated with a corresponding position and/or size of the iris and/or pupil. Noise may be canceled out by comparing signals from different photodiodes of the sensor. For example, a signal from a photodiode configured to receive light from (e.g., reflected from or transmitted through) one portion of the eye may be compared to a signal from a photodiode configured to receive light from (e.g., reflected from or transmitted through) another portion of the eye. As a further example, the light from a cornea/iris boundary may be relatively static because the cornea/iris boundary remains relatively static. Light from the pupil/iris boundary may change as the pupil/iris boundary changes to define the size of the pupil. The light from the cornea/iris boundary may be used as a reference to cancel out noise (e.g., changes in ambient lighting). For example, the system controller 114 may be configured to determine a ratio of signals from two different portions of the eye. As the ratio changes, for different photodiodes (e.g., or channels of photodiodes), the changing size of the pupil may be determined.

A power source 116 supplies power for numerous components comprising the non-contact sensor system. The power may be supplied from a battery, energy harvester, or other suitable means as is known to one of ordinary skill in the art. Essentially, any type of power source may be utilized to provide reliable power for all other components of the system. A sensor signal, processed from analog to digital, may enable activation of the system controller 114. Furthermore, the system controller 114 may control other aspects of a powered contact lens depending on input from the digital signal processor 108, for example, changing the focus or refractive power of an electronically controlled lens through an actuator 118.

In further alternate exemplary embodiments, the system controller 114 may receive input from sources including one or more of a vibration sensor, capacitance sensor, accelerometer, contact sensor, a blink detector, and a fob control. By way of generalization, it may be obvious to one skilled in the art that the method of activating and/or controlling the system controller 114 may require the use of one or more activation methods. For example, an electronic or powered contact lens may be programmable specific to an individual user, such as programming a lens to recognize a pupil size of an eye specific to the user. In some exemplary embodiments, using more than one method to activate an electronic contact lens, such as ciliary muscle signal detection and blink detection, may give the ability for each method to crosscheck with another before activation of the contact lens occurs. An advantage of crosschecking may include mitigation of false positives, such as minimizing the chance of unintentionally triggering a lens to activate.

In one exemplary embodiment, the crosschecking may involve a voting scheme, wherein a certain number of conditions are met prior to any action taking place. The actuator 118 may comprise any suitable device for implementing a specific action based upon a received command signal. The actuator 118 may comprise an electrical device, a mechanical device, a magnetic device or any combination thereof. The actuator 118 receives a signal from the system controller 114 in addition to power from the power source 116 and produces some action based on the signal from the system controller 114. For example, if the system controller 114 signal is indicative of the wearer trying to focus on a near object, the actuator 118 may be utilized to somehow change the refractive power of the electronic ophthalmic lens.

Figure 2:
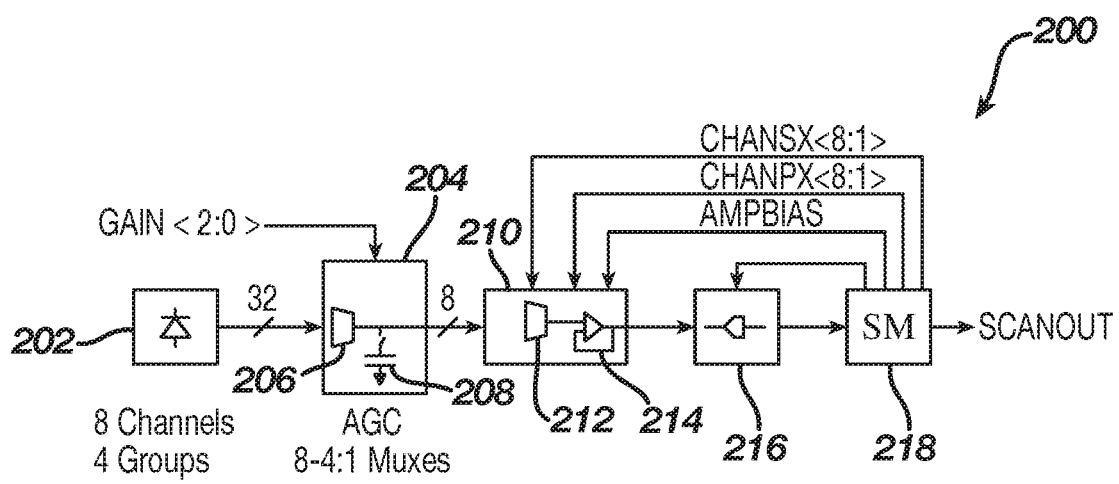
FIG. 2 illustrates an exemplary sensor in accordance with some embodiments of the present disclosure.

FIG. 2 illustrates an exemplary sensor 200 in accordance with some embodiments of the present disclosure. In an aspect, the sensor 200 may comprise a plurality of photodiodes 202. The plurality of photodiodes 202 may be organized in one or more groups and/or one or more channels. As an illustration, the plurality of photodiodes 202 may be organized as 8 channels. Each channel may comprise a portion of the plurality of diodes. Each channel may be associated with a corresponding direction and/or angle of incidence of light passing through a selection layer. The portion of the plurality of diodes may each be disposed to detect light from a corresponding direction and/or angle. For example, the portion of the plurality of diodes may comprise a row of diodes disposed at a similar or same distance from a slot of a selection layer (e.g., or an edge of a slot). The plurality of photodiodes 202 may be organized as 4 groups. The groups of the plurality of photodiodes may be associated with gain control. Output of different groups may be added and/or subtracted to perform gain control.

The sensor 200 may comprise an automatic gain control (AGC) unit 204. The AGC unit 204 may comprise a first multiplexer 206. The AGC unit 204 may comprise a capacitor 208. Though only one capacitor 208 is shown, it is understood that the sensor 200 may comprise multiple capacitors, such as one capacitor per channel, per group, or per photodiode. The capacitor 208 may carry a voltage. As light is detected by a photodiode, a charge may follow a path from the capacitor 208 (e.g., through the first multiplexer 206 and through the photodiode 202) to ground. The movement of the charge may change the voltage on the capacitor 208.

The sensor 200 may comprise a buffer amplifier unit 210. The buffer amplifier unit may comprise a second multiplexer 212. The buffer amplifier unit 210 may comprise a buffer amplifier 214.

The sensor 200 may comprise an analog-to-digital converter (ADC) 216. The ADC 216 may be configured to receive an analog signal from the buffer amplifier unit 210. The ADC 216 may be configured to convert the analog signal to a digital signal. The ADC 216 may output the digital signal. The digital signal may comprise a digital value indicative of an amount of light detected by one or more of the plurality of photodiodes (e.g., the photodiodes of a particular channel that is selected).

The sensor 200 may comprise a scanout unit 218. The scanout unit 218 may output the digital signal. The scanout unit 218 may be configured to output data indicative of a channel associated with the digital signal. For example, the digital signal may be combined with the data indicative of the channel associated with the digital signal.

The scanout unit 218 may be configured to supply an amp bias to the buffer amplifier 214. The amp bias may be configured to bias the buffer amplifier 214. The amp bias may comprise a voltage and/or current. The scanout unit 218 may be configured to supply a charge input (e.g., chanpx<8:1>). The charge input may be supplied to the buffer amplifier unit 210 (e.g., the second multiplexer 212, the buffer amplifier 214). The charge input may comprise an active low input (e.g., connection to ground). The charge input may be configured to cause a charge to be supplied to a particular channel. The scanout unit 218 may be configured to supply a selection input (e.g., chansx<8:1>). The selection input may be supplied to the buffer amplifier unit 210 (e.g., the second multiplexer 212, the buffer amplifier 214). The selection input may be configured to cause selection of a particular channel (e.g., to receive a signal from the channel). Selection of a channel may occur based on a predefined timing schedule. The selection input may comprise an active low input. The scanout unit 218 may be configured to supply an enable input to the ADC 216. The enable input may be configured to enable the ADC 216 to generate digital signals. As an illustration, the scanout unit 218 may be configured to operate several steps in succession for each channel. For example, the scanout unit 218 may be configured to scan each channel in succession for a signal (e.g., indicative of detection of light) by supplying the amp bias, supplying the charge input, supplying the selection input, and/or supplying the enable input.

Figure 3:
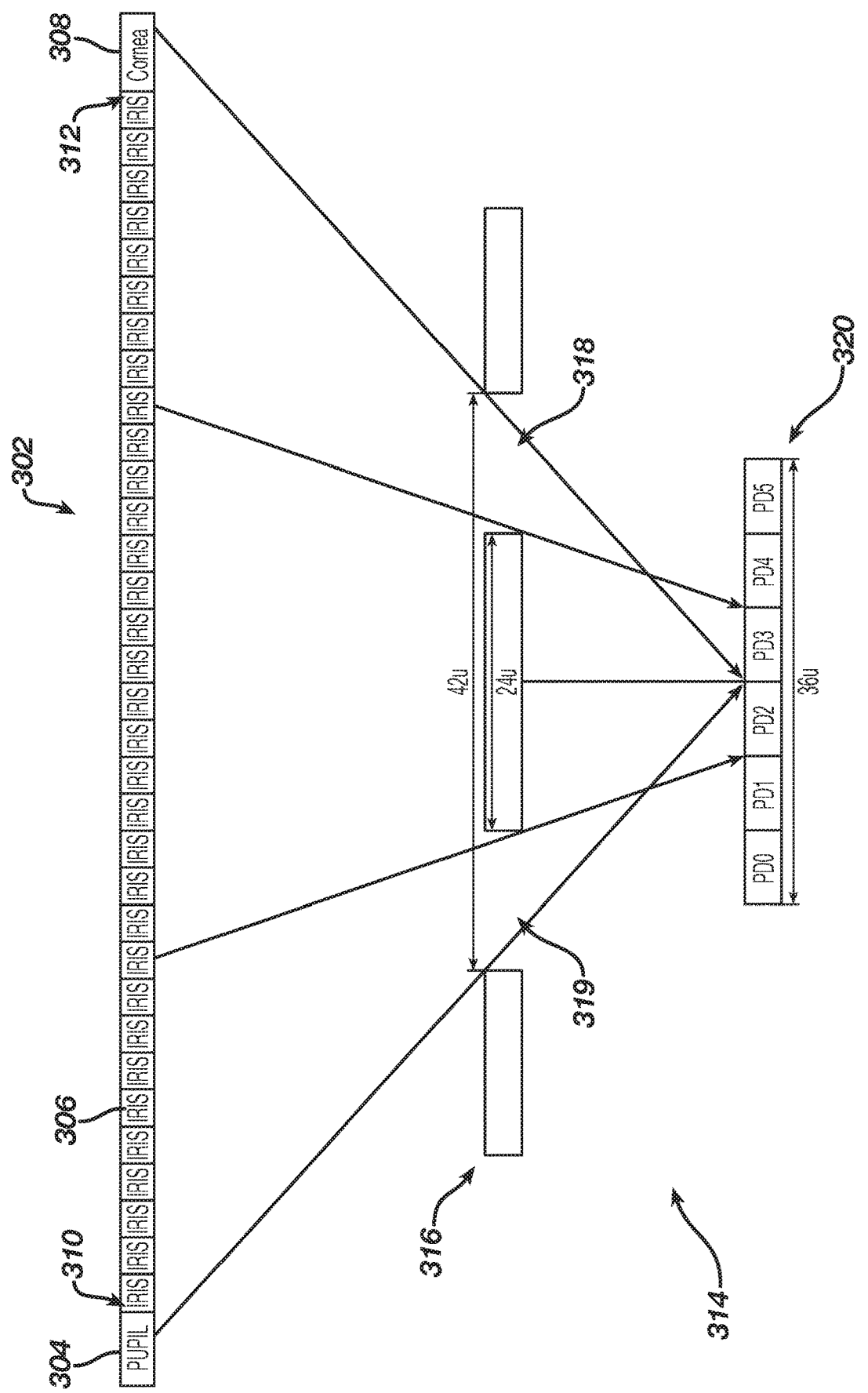
FIG. 3 illustrates detection of light from a variety of directions by a sensor in accordance with some embodiments of the present disclosure.

FIG. 3 illustrates detection of light from a variety of directions by a sensor in accordance with some embodiments of the present disclosure. A portion of an eye 302 of a user wearing an ophthalmic device is shown. The eye 302 may comprise a pupil 304, an iris 306, and a cornea 308. The eye 302 may comprise an iris-pupil boundary 310. The eye 302 may comprise an iris-cornea boundary 312.

In an aspect, a sensor 314 may be comprised in an ophthalmic device. The sensor 314 may be disposed to detect light from the eye 302. The sensor 314 may comprise a selection layer 316. The selection layer 316 may comprise one or more slots, such as a first slot 318 and a second slot 319. The one or more slots may comprise openings (e.g., gaps in the selection layer) that allow light from different directions to pass (e.g., be transmitted through) through the selection layer 316. The first slot 318 may be configured to allow light reflected from (e.g., or transmitted via) a portion of an iris near the cornea. A second slot 319 may be configured to allow light reflected from (e.g., or transmitted via) a portion of an iris near the pupil to pass through the selection layer 316. The one or more slots may have any appropriate dimension based on the angles and/or directions of light useful for a particular application.

The sensor 314 may comprise a plurality of photodiodes 320. The plurality of photodiodes 320. The plurality of photodiodes 320 may be arranged in a grid, as rows, as channels, and/or any other appropriate pattern. For example, each row of the plurality of photodiodes 320 may be a channel (e.g., PD0, PD1, PD2, PD3, PD4, PD5) of photodiodes. Each row and/or channel may be indicative of and/or associated with a direction and/or angle of light that passed through the selection layer. One or more rows and/or channels may be indicative of and/or associated with a size (e.g., diameter) of the iris and/or pupil.

Figure 4A:
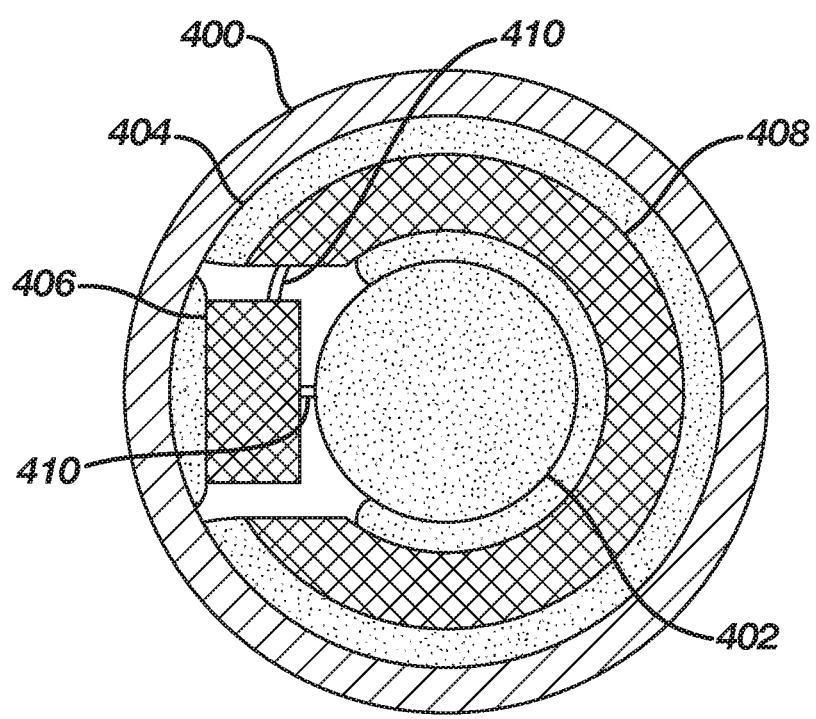
FIG. 4A is a planar view of an ophthalmic device comprising electronic components, including a sensor system and a variable-optic element in accordance with the present disclosure.

Referring now to FIG. 4A, there is illustrated, in planar view, a wearable electronic ophthalmic device comprising a sensor in accordance with the present disclosure. The ophthalmic device 400 comprises an optic zone 402 and a peripheral zone 404. The optic zone 402 may function to provide one or more of vision correction, vision enhancement, other vision-related functionality, mechanical support, or even a void to permit clear vision. In accordance with the present disclosure, the optic zone 402 may comprise a variable optic element configured to provide enhanced vision at near and distant ranges based on signals sensed from one or more sensors, such as those described herein. The variable-optic element may comprise any suitable device for changing the focal length of the lens or the refractive power of the lens based upon activation signals from the sensing system described herein. For example, the variable optic element may be as simple as a piece of optical grade plastic incorporated into the lens with the ability to have its spherical curvature changed. The peripheral zone 404 comprises one or more of electrical circuits 406, a power source 408, electrical interconnects 410, mechanical support, as well as other functional elements.

The electrical circuits 406 may comprise one or more integrated circuit die, printed electronic circuits, electrical interconnects, and/or any other suitable devices, including the sensing circuitry described herein. The power source 408 may comprise one or more of battery, energy harvesting, and or any other suitable energy storage or generation devices. It is readily apparent to the skilled artisan that FIG. 4A only represents one exemplary embodiment of an electronic ophthalmic lens and other geometrical arrangements beyond those illustrated may be utilized to optimize area, volume, functionality, runtime, shelf life as well as other design parameters. It is important to note that with any type of variable optic, the fail-safe is distance vision. For example, if power were to be lost or if the electronics fail, the wearer is left with an optic that allows for distance vision.

Figure 4B:
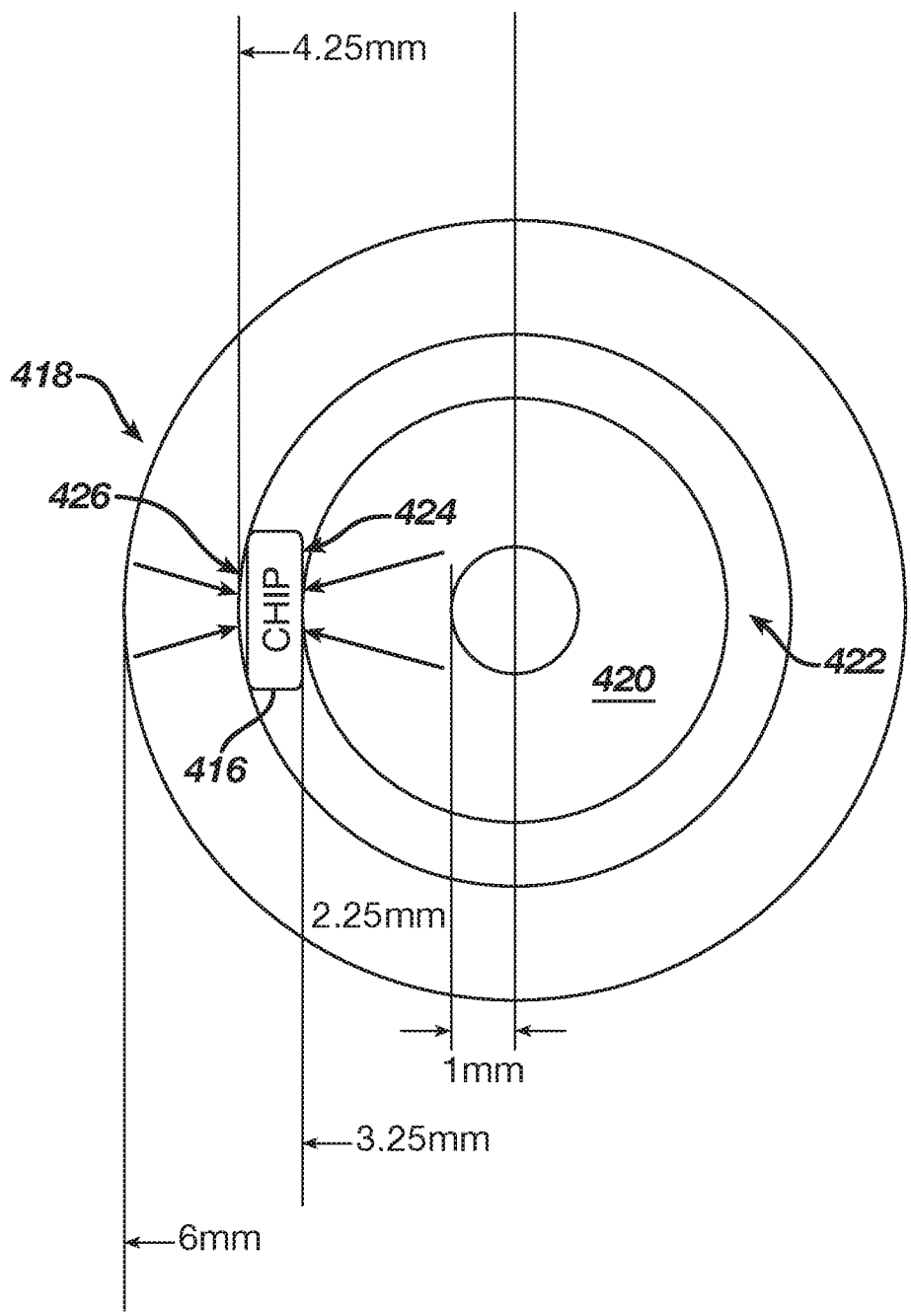
FIG. 4B illustrates location of an exemplary sensor in an ophthalmic device in accordance with some embodiments of the present disclosure.

FIG. 4B illustrates placement of an exemplary sensor in an ophthalmic device in accordance with some embodiments of the present disclosure. The sensor 416 may be disposed in an ophthalmic device 418, such as a contact lens or an intraocular lens. The ophthalmic device 418 may comprise an optic zone 420. The ophthalmic device 418 may comprise a peripheral zone 422. The sensor 416 may located in the peripheral zone 422. The sensor 416 may comprise a first side 424 and a second side 426. The first side 424 comprise a side of the plurality of photodiodes toward the pupil. The second side 426 may comprise a side of the plurality of photodiodes away from the pupil.

Figure 4C:
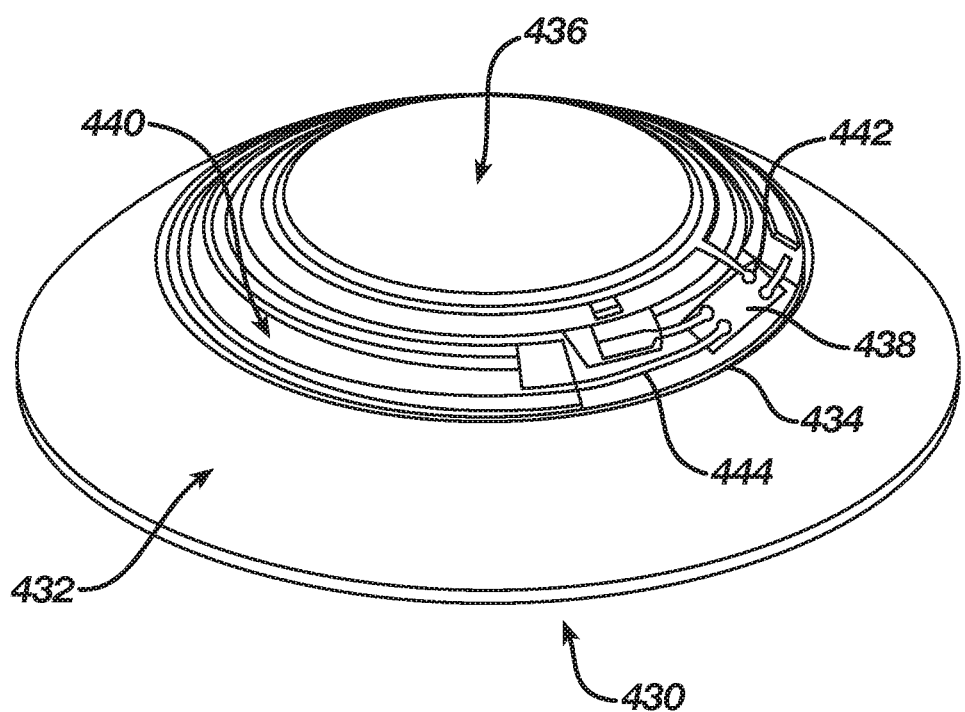
FIG. 4C is a diagrammatic representation of an exemplary powered or electronic ophthalmic device in accordance with the present disclosure.

FIG. 4C is a diagrammatic representation of an exemplary electronic insert, including a combined blink detection and communication system, positioned in a powered or electronic ophthalmic device in accordance with the present disclosure. As shown, a contact lens 430 comprises a soft plastic portion 432 which comprises an electronic insert 434. This insert 434 includes a lens 436 which is activated by the electronics, for example, focusing near or far depending on activation. Integrated circuit 438 mounts onto the insert 434 and connects to batteries 440, lens 436, and other components as necessary for the system. The integrated circuit 438 includes a sensor 442 and associated signal path circuits. The sensor 442 may comprise any sensor configuration such as those described herein. The sensor 442 may also be implemented as a separate device mounted on the insert 434 and connected with wiring traces 444.

Figure 5A:
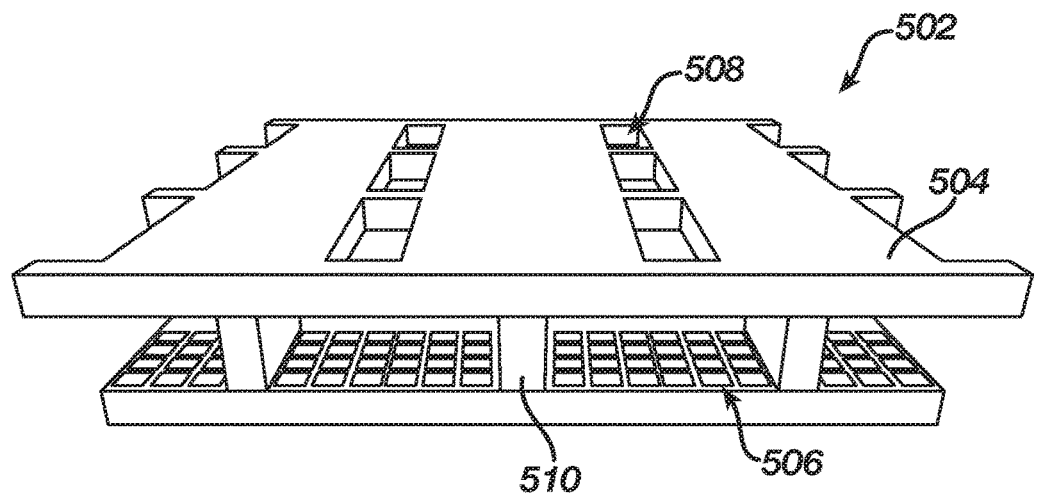
FIG. 5A is three-dimensional side view illustrating an exemplary sensor in accordance with some embodiments of the present disclosure.
Figure 5B:
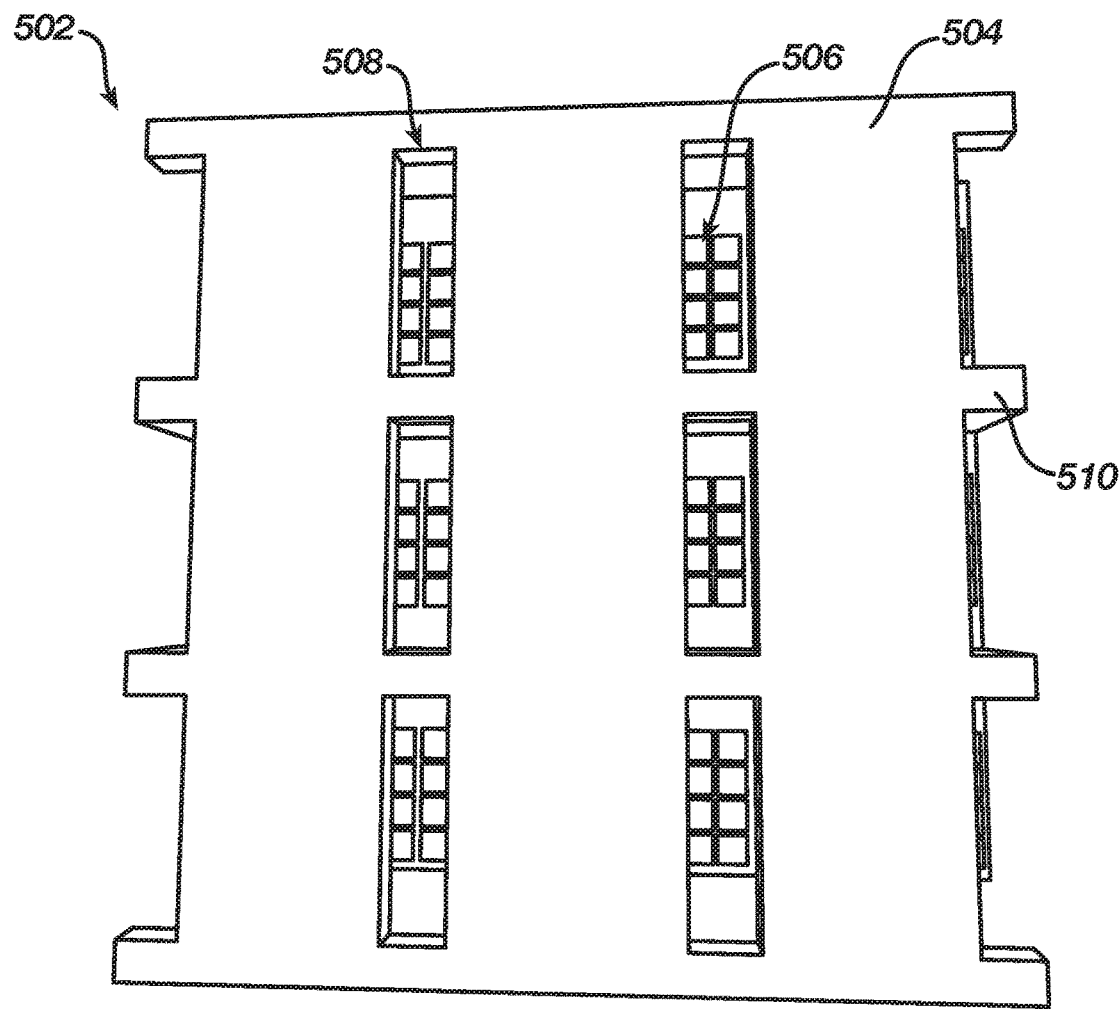
FIG. 5B is three-dimensional top-down view illustrating an exemplary sensor in accordance with some embodiments of the present disclosure.

FIG. 5A is three-dimensional side view illustrating an exemplary sensor in accordance with some embodiments of the present disclosure. FIG. 5B is three-dimensional top-down view illustrating an exemplary sensor in accordance with some embodiments of the present disclosure.

The sensor 502 may comprise a selection layer 504 and a plurality of photodiodes 506. The selection layer 504 may be disposed above the plurality of photodiodes 506. The section layer 504 may comprise a plurality of slots 508. A first portion of the plurality of slots 508 may be configured to allow light reflected from (e.g., or transmitted through) a portion of an iris near the cornea.

The plurality of photodiodes 506 may be arranged in a grid, as rows, and/or any other appropriate pattern. For example, each row of the plurality of photodiodes 506 may be a channel of photodiodes. Each row and/or channel may be indicative of and/or associated with a direction and/or angle of light that passed through the selection layer.

The plurality of slots 508 may have slots (e.g., or openings) that allow light to pass through from different directions. A first portion of the plurality of slots 508 may be configured to allow light reflected from (e.g., or transmitted through) a portion of an iris near the cornea. A second portion of the plurality of slots 508 may be configured to allow light reflected from (e.g., or transmitted through) a portion of an iris near the pupil. The slots may have an appropriate dimension based on the angles and/or directions of light useful for a particular application. The first portion may be separated from the second portion by a flange 510. The flange 510 may be attached to a substrate (e.g., layer of a circuit board).

Figure 5C:
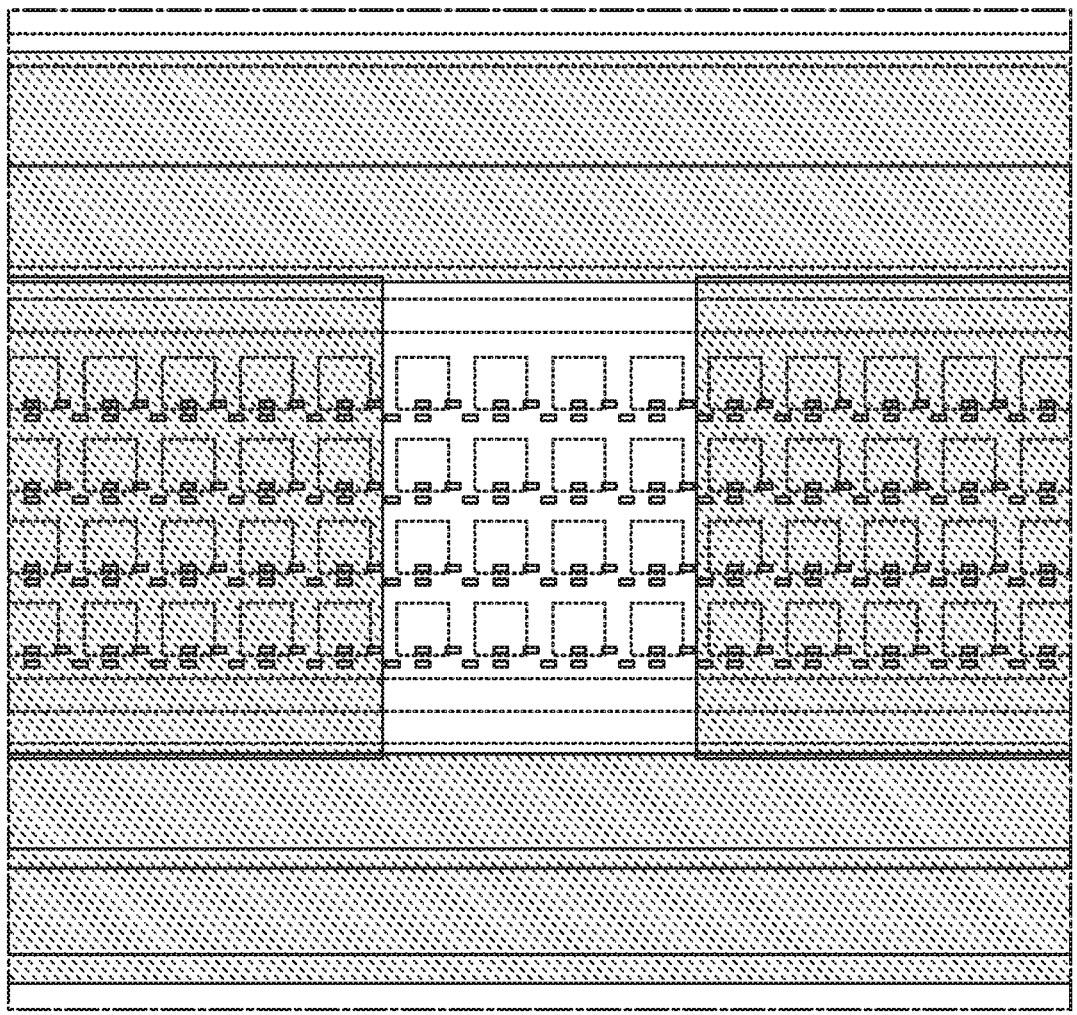
FIG. 5C is another top-down view illustrating an exemplary sensor in accordance with some embodiments of the present disclosure.

FIG. 5C is another top-down view illustrating an exemplary sensor in accordance with some embodiments of the present disclosure. As shown, some of the plurality of diodes may be directly under the slots in the selection layer. Other portions of the plurality of diodes may be offset from the opening (e.g., such that they only detect light below a corresponding angle). Photodiodes that are further from the slots may be associated with smaller angles of incidence.

FIG. 6A is a side view illustrating placement of a plurality of photodiodes of an exemplary sensor in accordance with some embodiments of the present disclosure. FIG. 6B is a top-down view illustrating placement of a plurality of photodiodes of an exemplary sensor in accordance with some embodiments of the present disclosure. The photodiodes may be organized in channels PD1, PD2, PD3, and PD4. Each of the channels may comprise a row of photodiode cells. Metal layers M1, M2, M3, M4, M5, M6, and LM may be disposed above the photodiode cells. M1 may comprise a bottom metal layer. M2 may comprise a second metal layer disposed above (e.g., directly above, on top of) M2. M3 may comprise a third metal layer disposed above (e.g., directly above, on top of) M2. M4 may comprise a fourth metal layer disposed above (e.g., directly above, on top of) M3. M5 may comprise a fifth metal layer disposed above (e.g., directly above, on top of) M4. M6 may comprise a sixth metal layer disposed above (e.g., directly above, on top of) M5. LM may comprise a last metal layer disposed above (e.g., directly above, on top of) M6. In an aspect, one or more of the metal layers M1, M2, M3, M4, M5, M6, and LM may comprise the selection layer described herein. As an example, LM may comprise the selection layer. M1, M2, M3, M4, M5, and/or M6 may comprise a support structure for the selection layer.

Figure 6C:
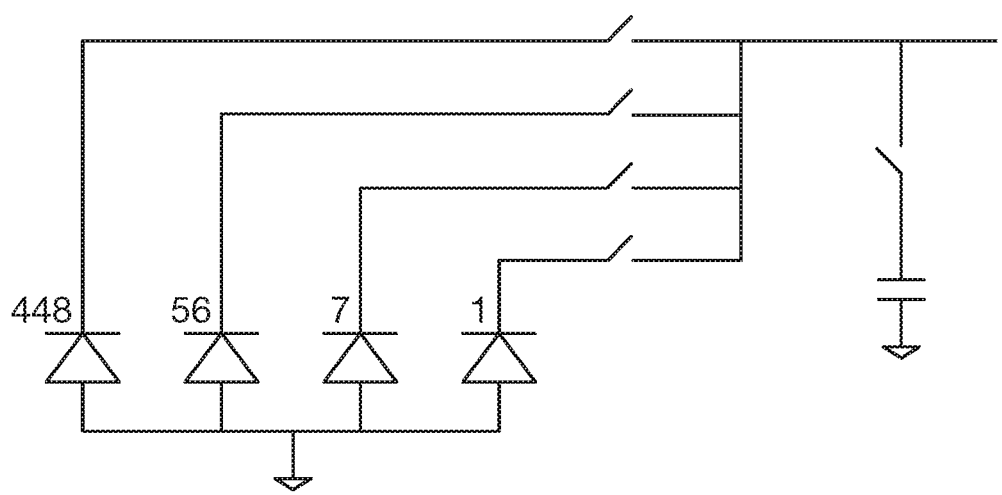
FIG. 6C is a circuit diagram illustrating an example channel of photodiodes in accordance with some embodiments of the present disclosure.

FIG. 6C is a circuit diagram illustrating an example channel of photodiodes in accordance with some embodiments of the present disclosure. In an aspect, a channel of photodiodes may comprise on or more photodiodes in parallel. The photodiodes may be electrically coupled (e.g., when switched on) to a capacitor. When the photodiodes are turned on in sequence, the photodiodes may add up to 8× binary steps, such as 1, 8, 64, 512, and/or the like.

Figure 7:
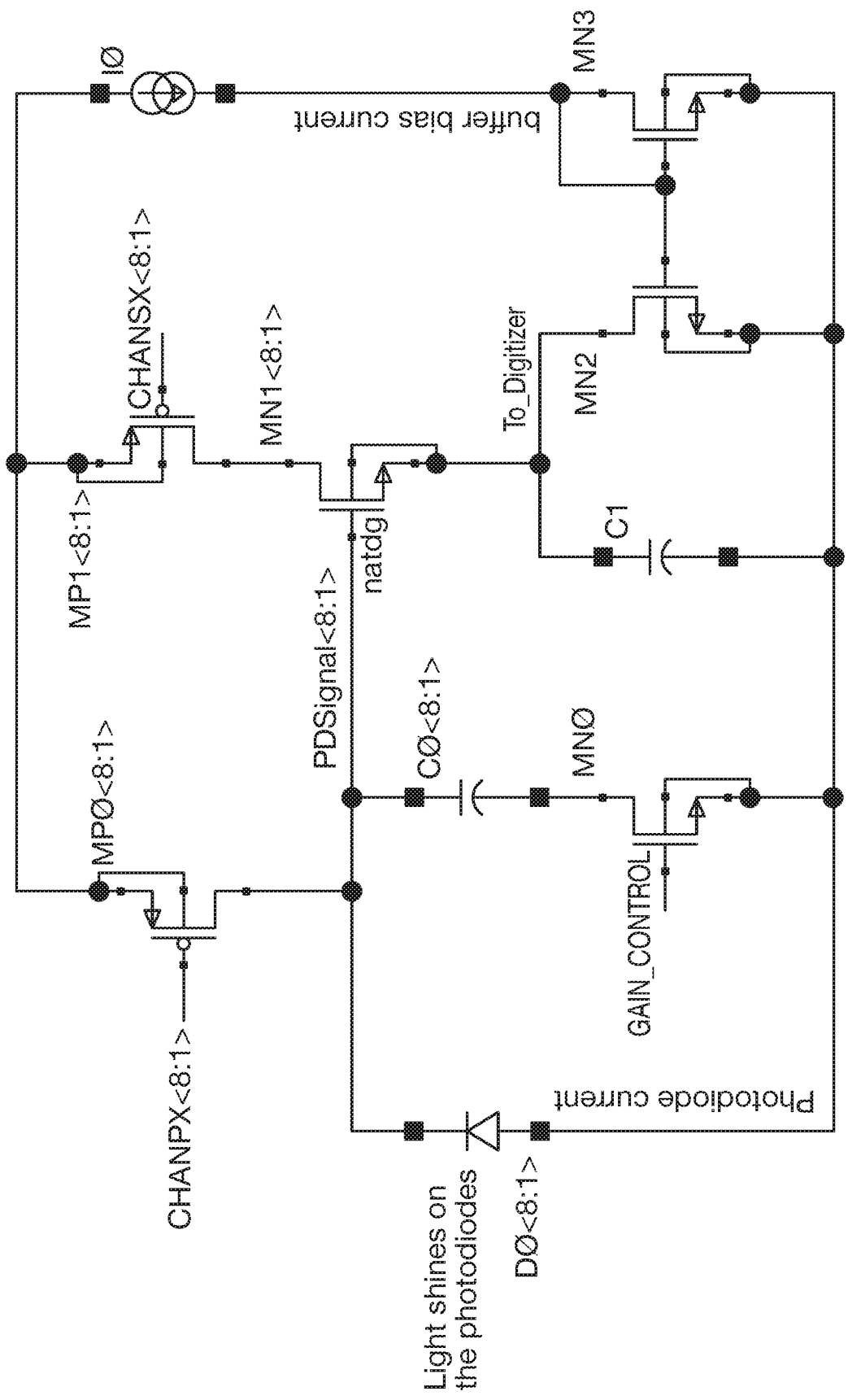
FIG. 7 is a circuit diagram illustrating an exemplary sensor in accordance with some embodiments of the present disclosure.
Figure 8:
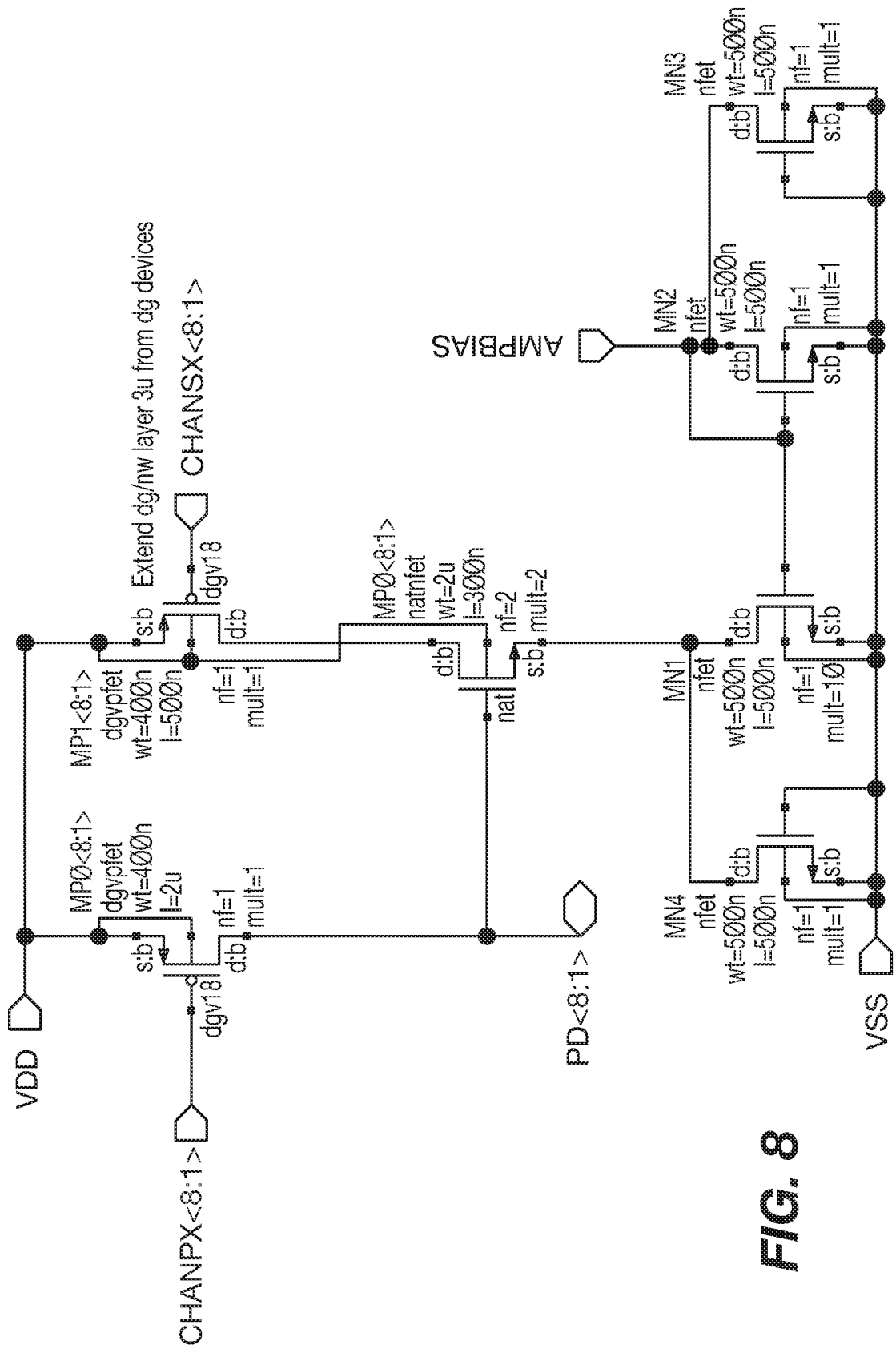
FIG. 8 is a circuit diagram illustrating a buffer amplifier of an exemplary sensor in accordance with some embodiments of the present disclosure.

FIG. 7 is a circuit diagram illustrating an exemplary sensor in accordance with some embodiments of the present disclosure. The sensor may comprise one or more photodiodes DO, which may be precharged by a precharge switch MP0. As light shines on the one or more photodiodes DO, current is created through DO. After a period of integration time, a channel select switch MP1 selects a channel buffer. A voltage generated on the gate of MN1 is indicative of a signal from the one or more photodiodes DO. MN1 may comprise a voltage follower amplifier configured to buffer the voltage. FIG. 8 is a circuit diagram illustrating a buffer amplifier of an exemplary sensor in accordance with some embodiments of the present disclosure. The buffer amplifier may comprise the precharge switch MP0, the channel select switch MP1, and a low voltage follower MN0.

Figure 9:
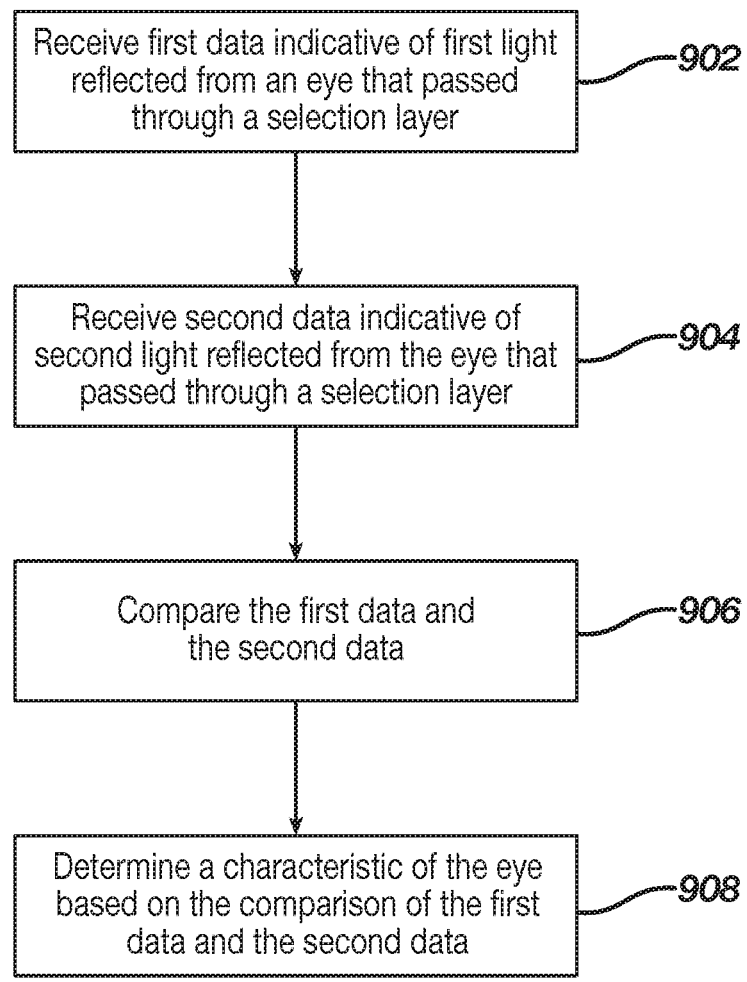
FIG. 9 is a flowchart illustrating an exemplary method in accordance with some embodiments of the present disclosure.

FIG. 9 is a flowchart illustrating an exemplary method in accordance with some embodiments of the present disclosure. At step 902, first data indicative of first light reflected from (e.g., or transmitted through) an eye that passed through a selection layer can be received. At step 904, second data indicative of second light reflected from the eye that passed through the selection layer may be received. The selection layer may be configured to reject (e.g., reflect, absorb) light reflected from (e.g., or transmitted through) the eye within a first range of incident angles and allow (e.g., transmit) light reflected from (e.g., or transmitted through) the eye within a second range of incident angles to pass through the selection layer to one or more of a plurality of photodiodes. The selection layer may comprise a metal wire layer. The metal wire layer may be configured to reject light within the first range of incident angles and allow light within the second range of incidence angles to pass through the selection layer. The selection layer may comprise a plurality of slots configured to reject light within the first range of incident angles and allow light within the second range of incidence angles to pass through the selection layer.

The selection layer and/or the plurality of photodiodes may be comprised in an ophthalmic device disposed in or on the eye. The ophthalmic device may comprise a contact lens or an intraocular lens. The contact lens may comprise a soft contact lens. The contact lens may comprise hybrid contact lens comprising a soft component (e.g., adjustable lens) and a hard component (e.g., processor, sensor).

At step 906, the first data and the second data may be compared.

At step 908, a characteristic of the eye may be determined. The characteristic of the eye may be determined based on the comparison of the first data and the second data. The characteristic of the eye may comprise impedance associated with a movement of a ciliary muscle of the eye, a focal distance of the eye, a size (e.g., diameter) of a pupil of the eye, a combination thereof, and/or the like.

As an example, the first light may be detected by a first photodiode of the plurality of photodiodes. The first photodiode may be one of a first region of the plurality of photodiodes that detects the first light. The second light may be detected by a second photodiode of the plurality of photodiodes. The second photodiode may be one of a second region of the plurality of photodiodes that detects the second light. The first light may be detected at the same time (e.g., a first time) as the second light. The first photodiode (e.g., first region of the plurality of photodiodes) may be configured to detect light reflected from (e.g., or transmitted through) a first boundary of an iris and a pupil of the eye. The second photodiode (e.g., second region of the plurality of photodiodes) may be configured to detect light reflected from (e.g., or transmitted through) a second boundary of the iris and a pupil of the eye. As another example, the second photodiode may be configured to detect light reflected from (e.g., or transmitted through) the iris (e.g., only from the iris) and/or the pupil (e.g., only from the pupil). The first data may be from the first region of the plurality of photodiodes. The second data may be from the second region of the plurality of photodiodes. Comparing the first data to the second data may comprise using the first data as a reference to filter noise from the second data. The noise may comprise changes in light unrelated to a change in a size of a pupil of the eye.

The first photodiode may be configured to detect light reflected from (e.g., or transmitted through) an iris of the eye at a first location within the plurality of photodiodes. The second photodiode may be configured to detect light reflected from (e.g., or transmitted through) the iris at a second location within the plurality of photodiodes. The first location may be closer to a pupil of the eye than the second location. The first location may comprise a side of the plurality of photodiodes toward the pupil. The second location may comprise a side of the plurality of photodiodes away from the pupil.

As another example, the first light may be detected by a first photodiode of the plurality of photodiodes at a first time. The second light may be detected by the first photodiode at a second time. Comparing the first data to the second data may comprise determining a difference between the first data and the second data. The difference may be indicative of a change in a size of a pupil of the eye.

As another example, comparing the first data and the second data may comprise determining a ratio of the first data and the second data. Determining the characteristic of the eye may comprise determining a change in a pupil diameter by comparing a difference between a first ratio and a second ratio. The first ratio may be based on the first data and the second data. The second ratio may comprise a prior ratio determined before the first ratio.

Figure 10:
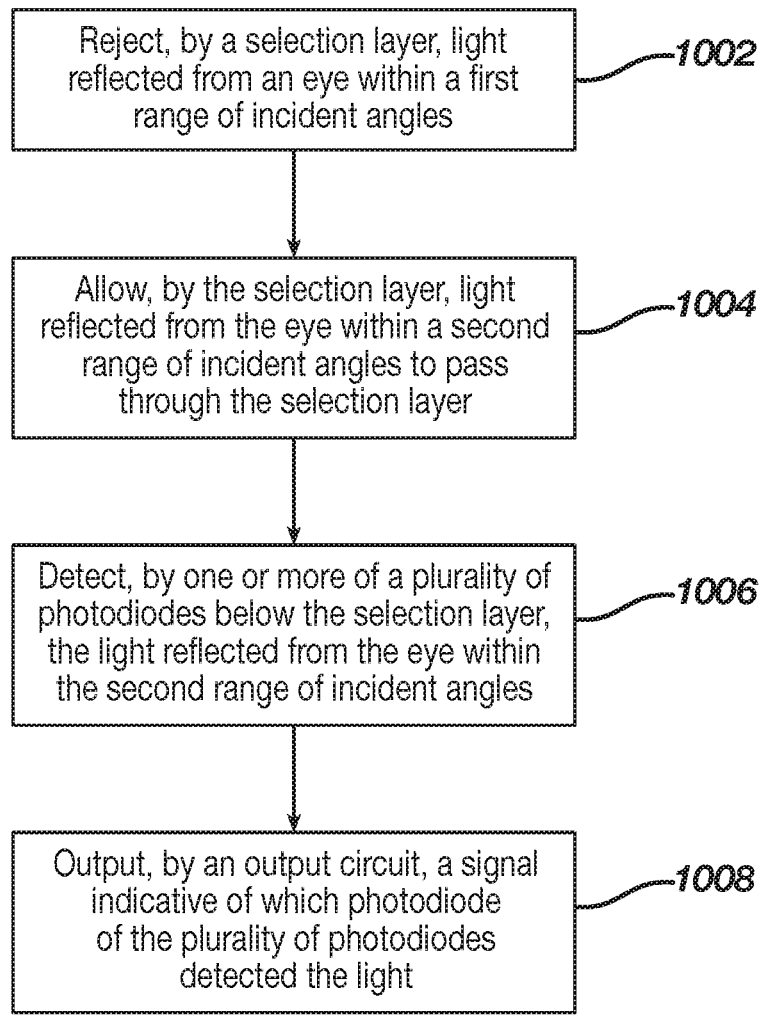
FIG. 10 is a flowchart illustrating another exemplary method in accordance with some embodiments of the present disclosure.

FIG. 10 is a flowchart illustrating another exemplary method in accordance with some embodiments of the present disclosure. At step 1002, light reflected from (e.g., or transmitted through) an eye within a first range of incident angles may be rejected (e.g., reflected, absorbed) by a selection layer. The selection layer may comprise a metal wire layer having metal wires separated by gaps in the selection layer. The metal wire layer may be configured to reject light within the first range of incident angles and allow light within the second range of incidence angles to pass through the selection layer The selection layer may comprise a plurality of slots configured to reject (e.g., reflect, absorb) the light reflected from (e.g., or transmitted through) the eye within the first range of incident angles and allow (e.g., transmit) the light reflected from (e.g., or transmitted through) the eye within the second range of incidence angles to pass through the selection layer.

At step 1004, light reflected from (e.g., or transmitted through) the eye within a second range of incident angles may be allowed to pass (e.g., transmitted through) through the selection layer. For example, the slots of the selection layer may be openings in the selection layer through which light within the second range of incident angles is able to pass.

At step 1006, the light reflected from (e.g., or transmitted through) the eye within the second range of incident angles may be detected by one or more of a plurality of photodiodes. The plurality of photodiodes may be below the selection layer. In an aspect, the plurality of photodiodes may be arranged by channels. The one or more of the plurality of photodiodes may be offset (e.g., along an axis extending parallel to and/or between the plurality of photodiodes and the selection layer) from the slots in the selection layer. The amount of the offset may be indicative of an angle and/or direction of the light. For example, the photodiodes may be organized as a plurality of rows and/or channels. Each row and/or channel may have a different offset from one or more slots or openings in the selection layer.

At step 1008, a signal indicative of which photodiode of the plurality of photodiodes detected the light may be output by an output circuit electrically coupled to the plurality of photodiodes. The output circuit may comprise a multiplexer electrically coupled to the channels. The output circuit may comprise an automatic gain controller comprising a plurality of groups of bits. Each group of bits may be dedicated to a corresponding channel. The automatic gain controller may comprise, for example, 25 control bits with 3 bits per channel. The automatic gain controller may be supplied a gain clock signal, a gain input signal, and/or the like. A photodiode enable signal may reset all bits to zero. The automatic gain controller may be configured to adjust the number of photodiodes used based on light levels (e.g., ambient light levels). For example, if light levels are low more photodiodes are used to increase the resulting signal. If light levels are high, fewer diodes may be used to decrease the signal levels. The number of photodiodes used may be determined to match a resulting photodiode current to an integrator capacitance.

The method 1000 may further comprise determining an environmental characteristic. The environmental characteristic may comprise a characteristic of a user. The environmental characteristic may be determined by analyzing the signal output from the output circuit and comparing a result of the analysis to data related to a prior signal. The environmental characteristic may be determined by analyzing the signal output from the output circuit to determine a direction of the light detected. The direction may be compared to a direction associated with light detected at another photodiode of the plurality of photodiodes.

In an aspect, outputting the signal indicative of which photodiode of the plurality of photodiodes detected the light may comprise outputting a channel number of the photodiode detecting the light. Outputting the signal indicative of which photodiode of the plurality of photodiodes detected the light may comprise outputting a digital signal based on light detected by one or more photodiodes of the plurality of photodiodes. The signal indicative of which photodiode of the plurality of photodiodes detected the light may comprise a signal indicative of a location of the photodiode.

The output circuit may comprise a buffer. The buffer may comprise a buffer amplifier. The output circuit may be configured to sequentially output a signal from each of the channels to the buffer. The buffer may output an amplified signal to an analog-to-digital converter.

The selection layer, the plurality of photodiodes, the output circuit, or a combination thereof may be disposed in or on an ophthalmic device, such as an electronic ophthalmic device. The ophthalmic device com may comprise a contact lens or an intraocular lens. The contact lens may comprise a soft contact lens. The contact lens may comprise a hybrid contact lens comprising a soft component and a hard component.

Figure 11A:
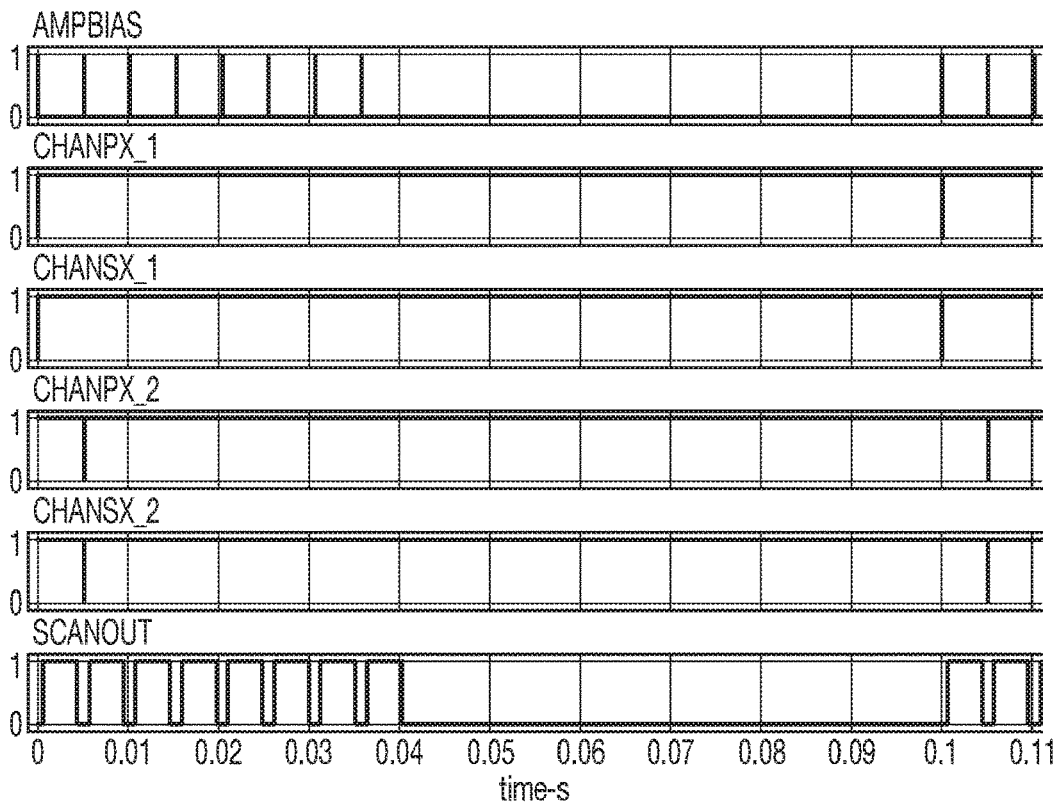
FIG. 11A is a graph illustrating operation of an exemplary sensor in accordance with some embodiments of the present disclosure.
Figure 11B:
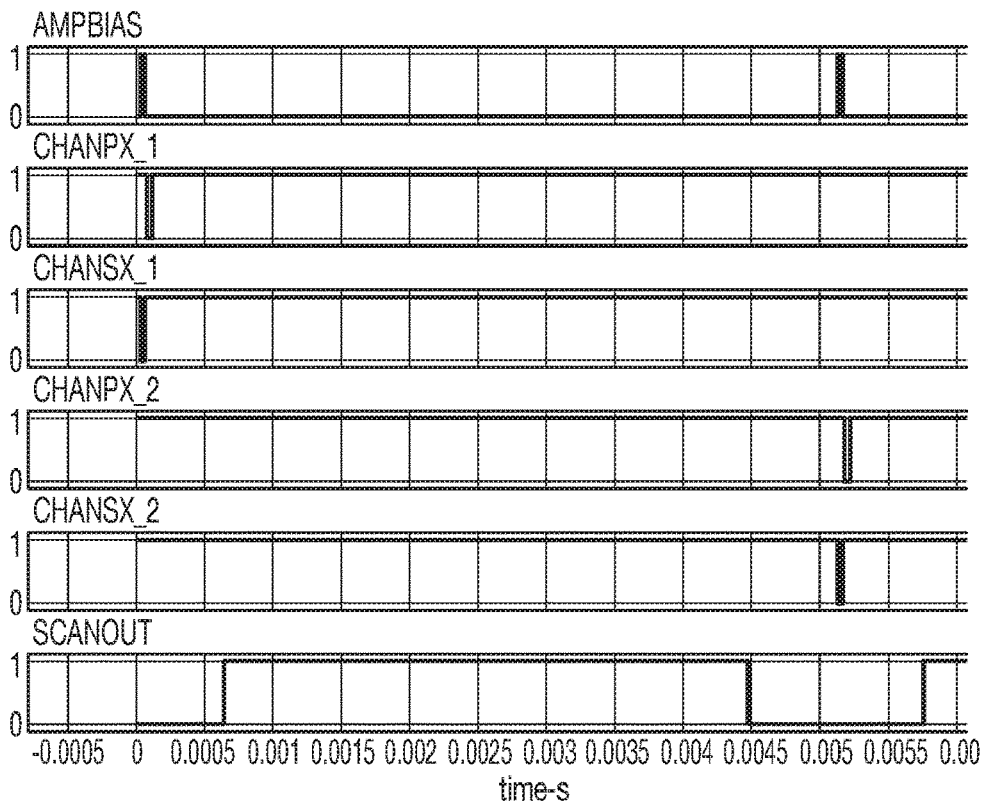
FIG. 11B is another graph illustrating operation of an exemplary sensor in accordance with some embodiments of the present disclosure.
Figure 11C:
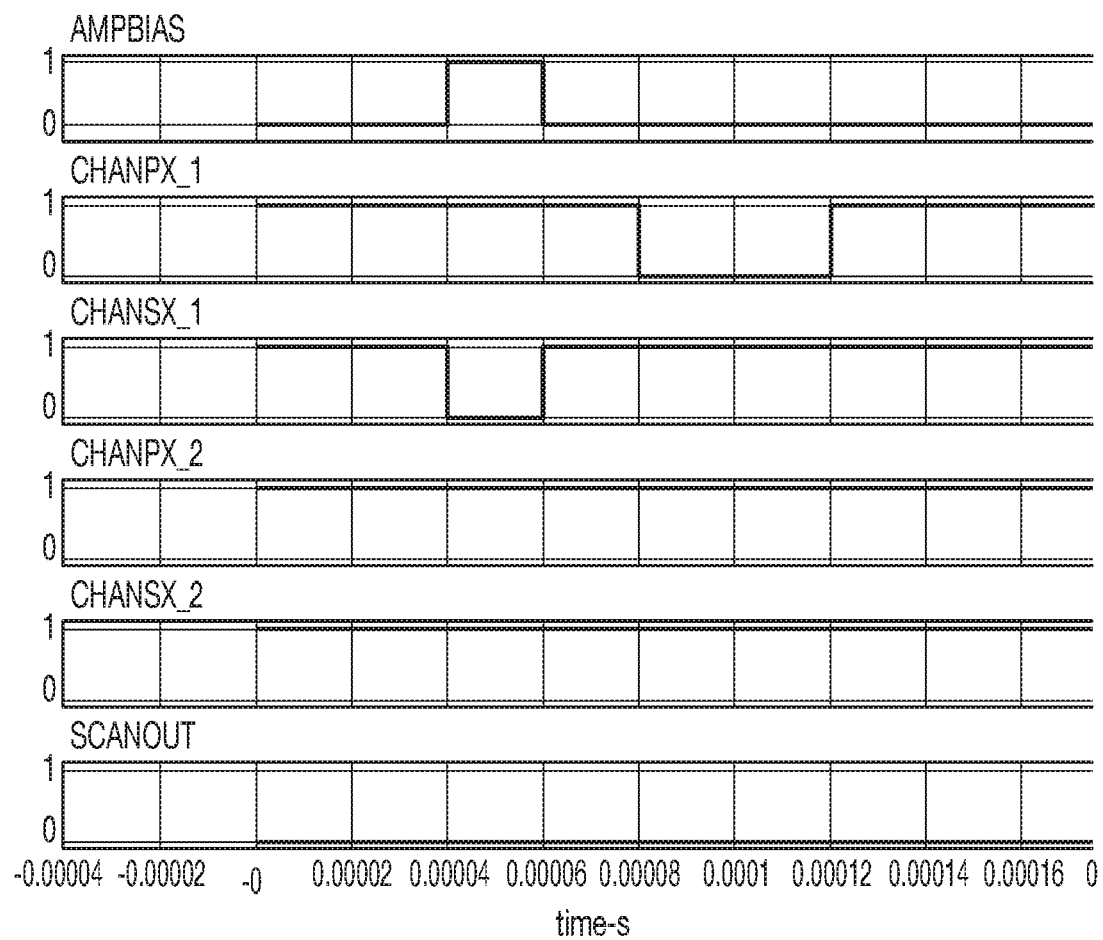
FIG. 11C is another graph illustrating operation of an exemplary sensor in accordance with some embodiments of the present disclosure.

FIGS. 11A-11C show example sequences of signals to operate an example output circuit. A variety of signals are shown for different portions of the sensor. FIG. 11A illustrates control signals for an 8 channel directional photodiode system. The control signals may comprise an ampbias signal supplied to the buffer amplifier to bias the amplifier. The control signals may comprise a first charge signal CHANPX_1 to charge a first channel of photodiodes. The control signals may comprise a first selection signal CHANSX_1 to select an output of the first channel of photodiodes. The control signals may comprise a second charge signal CHANPX_2 to charge a second channel of photodiodes. The control signals may comprise a second selection signal CHANSX_2 to select an output of the second channel of photodiodes. An output signal SCANOUT may comprise a signal output from the output circuit.

FIG. 11B illustrates activation (e.g., simultaneously or at least partially or substantially at the same time) of the ampbias signal and selection signals (e.g., first selection signal and second selection signal). Simultaneous activation of the ampbias signal and the first selection signal CHANSX_1 buffers the photodiode signal for channel 1 so that photodiode signal can be digitized. After conversion, the first charge signal CHANPX_1 is activated to precharge channel 1 for another conversion. Subsequently, the ampbias signal is activated along with the second selection signal CHANSX_2 to buffer the photodiode signal for channel 2 for digitization. After conversion, the second charge signal CHANPX_2 is activated to precharge channel 2 for another conversion.

The following tables illustrates example specifications of a sensor as described herein. It should be understood that the example specifications are non-limiting and only describe an example embodiment for purposes of illustration. Table 1 illustrates Pupil Diameter specifications. Table 2 illustrates directional photodiode Buffer Amp specifications. Table 3 illustrates automatic gain control specifications.

TABLE 1

| Parameter | Min | Typ | Max | Units |
|---|---|---|---|---|
| Active Current | | 1 | | uA |
| Supply | 0.99 | 1.1 | 1.21 | V |
| Sample Rate | | 10 | | Hz |
| 5 Gain Ranges* | 0.0004 | | 108 | $W/m^2$ |
| 8 Channels | | | | |
| SCANOUT Rate | | 4 | | kHz |
| ADC Load on Buffer AMP | | | 5 | pF |

*Min is most sensitive range/128
*Max is full scale of the least sensitive range.

TABLE 2

| Parameter | Min | Typ | Max | Units |
|---|---|---|---|---|
| Supply | 0.99 | 1.1 | 1.21 | V |
| Bias | 0.8 | 1 | 1.2 | uA |
| Load | | | 5 | pF |
| Settle Time | 10 | 16 | | uS |
| Charge Time | 10 | 16 | | uS |

TABLE 3

| Gain | No. of photodiodes | Added Capacitance | Min Sense $w/m^2$ | Max Sense $w/m^2$ |
|---|---|---|---|---|
| 000 | 512 | 0 | 0.2 m | 0.05 |
| 001 | 512 | 9 pF | 0.8 m | 0.2 |
| 010 | 64 | 9 pF | 6.8 m | 1.7 |
| 011 | 8 | 9 pF | 54 m | 13.5 |
| 100 | 1 | 9 pF | 423 m | 108.2 |

Although shown and described in what is believed to be the most practical and preferred embodiments, it is apparent that departures from specific designs and methods described and shown will suggest themselves to those skilled in the art and may be used without departing from the spirit and scope of the disclosure. The present disclosure is not restricted to the particular constructions described and illustrated but rather encompasses any and all modifications that may fall within the scope of the appended claims.

What is claimed is:

1. An ophthalmic system comprising:
an ophthalmic device configured to be disposed within or upon an eye of a user; and
a sensor system disposed in or on the ophthalmic device, the sensor system comprising:
a sensor comprising:
a selection layer configured to receive light from the eye, wherein the selection layer is configured to reject light from the eye within a first range of incident angles and allow light from the eye within a second range of incident angles to pass through the selection layer; and
a plurality of photodiodes disposed below the selection layer and configured to detect the light from the eye that is allowed to pass through the selection layer; and
a processor operably connected to the sensor and configured for:
receiving first data indicative of first light from the eye that passed through the selection layer;
receiving second data indicative of second light from the eye that passed through the selection layer;
comparing the first data and the second data; and
determining a characteristic of the eye based on the comparison of the first data and the second data.

2. The ophthalmic system of claim 1, wherein the first light is detected by a first photodiode of the plurality of photodiodes and wherein the second light is detected by a second photodiode of the plurality of photodiodes.

3. The ophthalmic system of claim 2, wherein the first photodiode is configured to detect light from a first boundary of an iris and a pupil of the eye and the second photodiode is configured to detect light from one or more of the iris or the pupil.

4. The ophthalmic system of claim 2, wherein comparing the first data to the second data comprises using the first data as a reference to filter noise from the second data, wherein the noise comprises changes in light unrelated to a change in a size of a pupil of the eye.

5. The ophthalmic system of claim 2, wherein the first photodiode is configured to detect light from an iris of the eye at a first location of the sensor, and wherein the second photodiode is configured to detect light from the iris at a second location of the sensor, wherein the first location is closer to a pupil of the eye than the second location.

6. The ophthalmic system of claim 5, wherein the first location comprises a side of the sensor toward the pupil and the second location comprises a side of the sensor away from the pupil.

7. The ophthalmic system of claim 1, wherein the first light is detected by a first photodiode of the plurality of photodiodes at a first time and wherein the second light is detected by the first photodiode at a second time.

8. The ophthalmic system of claim 7, wherein comparing the first data to the second data comprises determining a difference between the first data and the second data, wherein the difference is indicative of a change in a size of a pupil of the eye.

9. The ophthalmic system of claim 1, wherein the first light is detected by a first photodiode of the plurality of photodiodes at a first time, and wherein the second light is detected by a second photodiode at the first time.

10. The ophthalmic system of claim 1, wherein the characteristic of the eye comprises a focal distance of the eye.

11. The ophthalmic system of claim 1, wherein the characteristic of the eye comprises a size of a pupil of the eye.

12. The ophthalmic system of claim 1, wherein the selection layer comprises a metal wire layer configured to reject light within the first range of incident angles and allow light within the second range of incidence angles to pass through the selection layer.

13. The ophthalmic system of claim 1, wherein the selection layer comprises a plurality of slots configured to reject light within the first range of incident angles and allow light within the second range of incidence angles to pass through the selection layer.

14. The ophthalmic system of claim 1, wherein comparing the first data and the second data comprises determining a ratio of the first data and the second data.

15. The ophthalmic system of claim 1, wherein determining the characteristic of the eye comprises determining a change in a pupil diameter by comparing a difference between a first ratio and a second ratio, wherein the first ratio is based on the first data and the second data, and wherein the second ratio comprises a prior ratio determined before the first ratio.

16. The ophthalmic system of claim 1, wherein the ophthalmic device comprises a contact lens or an intraocular lens.

17. The ophthalmic system of claim 16, wherein the contact lens comprises a soft contact lens or a hybrid contact lens comprising a soft component and a hard component.

18. The ophthalmic system of claim 1, wherein the light from the eye comprises light that is one or more of reflected from the eye or transmitted through the eye.

19. A method comprising:
receiving first data indicative of first light from an eye that passed through a selection layer, wherein the selection layer is configured to reject light from the eye within a first range of incident angles and allow light from the eye within a second range of incident angles to pass through the selection layer to one or more of a plurality of photodiodes, wherein the selection layer and the plurality of photodiodes are comprised in an ophthalmic device disposed in or on the eye;
receiving second data indicative of second light from the eye that passed through the selection layer;
comparing the first data and the second data; and
determining a characteristic of the eye based on the comparison of the first data and the second data.

20. The method of claim 19, wherein the first light is detected by a first photodiode of the plurality of photodiodes and wherein the second light is detected by a second photodiode of the plurality of photodiodes.

21. The method of claim 20, wherein the first photodiode is configured to detect light from a first boundary of an iris and a pupil of the eye and the second photodiode is configured to detect light from one or more of the iris or the pupil.

22. The method of claim 20, wherein comparing the first data to the second data comprises using the first data as a reference to filter noise from the second data, wherein the noise comprises changes in light unrelated to a change in a size of a pupil of the eye.

23. The method of claim 20, wherein the first photodiode is configured to detect light from an iris of the eye at a first location within the plurality of photodiodes, and wherein the second photodiode is configured to detect light from the iris at a second location within the plurality of photodiodes, wherein the first location is closer to a pupil of the eye than the second location.

24. The method of claim 23, wherein the first location comprises a side of the plurality of photodiodes toward the pupil and the second location comprises a side of the plurality of photodiodes away from the pupil.

25. The method of claim 19, wherein the first light is detected by a first photodiode of the plurality of photodiodes at a first time and wherein the second light is detected by the first photodiode at a second time.

26. The method of claim 25, wherein comparing the first data to the second data comprises determining a difference between the first data and the second data, wherein the difference is indicative of a change in a size of a pupil of the eye.

27. The method of claim 19, wherein the first light is detected by a first photodiode of the plurality of photodiodes at a first time, and wherein the second light is detected by a second photodiode of the plurality of photodiodes at the first time.

28. The method of claim 19, wherein the characteristic of the eye comprises a focal distance of the eye.

29. The method of claim 19, wherein the characteristic of the eye comprises a size of a pupil of the eye.

30. The method of claim 19, wherein the selection layer comprises a metal wire layer configured to reject light within the first range of incident angles and allow light within the second range of incidence angles to pass through the selection layer.

31. The method of claim 19, wherein the selection layer comprises a plurality of slots configured to reject light within the first range of incident angles and allow light within the second range of incidence angles to pass through the selection layer.

32. The method of claim 19, wherein comparing the first data and the second data comprises determining a ratio of the first data and the second data.

33. The method of claim 19, wherein determining the characteristic of the eye comprises determining a change in a pupil diameter by comparing a difference between a first ratio and a second ratio, wherein the first ratio is based on the first data and the second data, and wherein the second ratio comprises a prior ratio determined before the first ratio.

34. The method of claim 19, wherein the ophthalmic device comprises a contact lens or an intraocular lens.

35. The method of claim 34, wherein the contact lens comprises a soft contact lens or a hybrid contact lens comprising a soft component and a hard component.

36. The method of claim 19, wherein the light from the eye comprises light that is one or more of reflected from the eye or transmitted through the eye.

37. A sensor comprising:
a selection layer configured to be disposed in or on an ophthalmic device to receive light from an eye, wherein the selection layer is configured to reject light from the eye within a first range of incident angles and allow light from the eye within a second range of incident angles to pass through the selection layer;
a plurality of photodiodes disposed below the selection layer and configured to detect the light from the eye within the second range of incident angles that is allowed to pass through the selection layer; and
an output circuit electrically coupled to the plurality of photodiodes and configured to output a signal indicative of which photodiode of the plurality of photodiodes detected the light.

38. The sensor of claim 37, wherein the ophthalmic device comprises a contact lens or an intraocular lens.

39. The sensor of claim 38, wherein the contact lens comprises a soft contact lens or a hybrid contact lens comprising a soft component and a hard component.

40. The sensor of claim 37, wherein the plurality of photodiodes are arranged by channels.

41. The sensor of claim 40, wherein the output circuit comprises a multiplexer electrically coupled to the channels.

42. The sensor of claim 41, wherein the output circuit comprises an automatic gain controller comprising a plurality of groups of bits, wherein each group of bits is dedicated to a corresponding channel.

43. The sensor of claim 37, wherein the selection layer comprises a metal wire layer having metal wires separated by gaps in the selection layer, wherein the metal wire layer is configured to reject light within the first range of incident angles and allow light within the second range of incidence angles to pass through the selection layer.

44. The sensor of claim 37, wherein the selection layer comprises a plurality of slots configured to reject the light from the eye within the first range of incident angles and allow the light from the eye within the second range of incidence angles to pass through the selection layer.

45. The sensor of claim 37, wherein output circuit is configured to output a channel number of the photodiode detecting the light.

46. The sensor of claim 37, wherein the signal indicative of which photodiode of the plurality of photodiodes detected the light comprises a signal indicative of a location of the photodiode.

47. The sensor of claim 37, wherein the output circuit is configured to output a digital signal based on light detected by one or more photodiodes of the plurality of photodiodes.

48. The sensor of claim 37, further comprising a processor configured to determine an environmental characteristic by analyzing the signal output from the output circuit and comparing a result of the analysis to data related to a prior signal.

49. The sensor of claim 37, further comprising a processor configured to determine an environmental characteristic by analyzing the signal output from the output circuit to determine a direction of the light detected and comparing the direction to a direction associated with light detected at another photodiode of the plurality of photodiodes.

50. The sensor of claim 37, wherein the output circuit comprises a buffer.

51. The sensor of claim 37, wherein the light from the eye comprises light that is one or more of reflected from the eye or transmitted through the eye.

52. A method comprising:
    rejecting, by a selection layer, light from an eye within a first range of incident angles, wherein the selection layer is disposed in or on an ophthalmic device;
    allowing, by the selection layer, light from the eye within a second range of incident angles to pass through the selection layer;
    detecting, by one or more of a plurality of photodiodes below the selection layer, the light from the eye within the second range of incident angles; and
    outputting, by an output circuit electrically coupled to the plurality of photodiodes, a signal indicative of which photodiode of the plurality of photodiodes detected the light.

53. The method of claim 52, wherein the ophthalmic device comprises a contact lens or an intraocular lens.

54. The method of claim 53, wherein the contact lens comprises a soft contact lens or a hybrid contact lens comprising a soft component and a hard component.

55. The method of claim 52, wherein the plurality of photodiodes are arranged by channels.

56. The method of claim 55, wherein the output circuit comprises a multiplexer electrically coupled to the channels.

57. The method of claim 56, wherein the output circuit comprises an automatic gain controller comprising a plurality of groups of bits, wherein each group of bits is dedicated to a corresponding channel.

58. The method of claim 52, wherein the selection layer comprises a metal wire layer having metal wires separated by gaps in the selection layer, wherein the metal wire layer is configured to reject light within the first range of incident angles and allow light within the second range of incidence angles to pass through the selection layer.

59. The method of claim 52, wherein the selection layer comprises a plurality of slots configured to reject the light from the eye within the first range of incident angles and allow the light from the eye within the second range of incidence angles to pass through the selection layer.

60. The method of claim 52, wherein outputting the signal indicative of which photodiode of the plurality of photodiodes detected the light comprises outputting a channel number of the photodiode detecting the light.

61. The method of claim 52, wherein the signal indicative of which photodiode of the plurality of photodiodes detected the light comprises a signal indicative of a location of the photodiode.

62. The method of claim 52, wherein outputting the signal indicative of which photodiode of the plurality of photodiodes detected the light comprises outputting a digital signal based on light detected by one or more photodiodes of the plurality of photodiodes.

63. The method of claim 52, further comprising determining an environmental characteristic by analyzing the signal output from the output circuit and comparing a result of the analysis to data related to a prior signal.

64. The method of claim 52, further comprising:
    determining an environmental characteristic by analyzing the signal output from the output circuit to determine a direction of the light detected; and
    comparing the direction to a direction associated with light detected at another photodiode of the plurality of photodiodes.

65. The method of claim 52, wherein the output circuit comprises a buffer.

66. The method of claim 52, wherein the light from the eye comprises light that is one or more of reflected from the eye or transmitted through the eye.

* * * * *